(12) United States Patent
Anderson

(10) Patent No.: US 7,026,941 B1
(45) Date of Patent: Apr. 11, 2006

(54) SYSTEM AND METHOD FOR MEASURING A PLURALITY OF PHYSICAL VARIABLES FROM A REMOTE LOCATION

(75) Inventor: John William Crisman Anderson, Louisville, KY (US)

(73) Assignee: NetQuest Services, LLC, Louisville, KY (US)

( * ) Notice: Subject to any disclaimer, the term of this patent is extended or adjusted under 35 U.S.C. 154(b) by 0 days.

(21) Appl. No.: 10/812,670

(22) Filed: Mar. 30, 2004

Related U.S. Application Data

(63) Continuation of application No. 10/086,475, filed on Mar. 1, 2002, now abandoned.

(60) Provisional application No. 60/272,679, filed on Mar. 1, 2001.

(51) Int. Cl.
| | |
|---|---|
| G08B 13/14 | (2006.01) |
| G08B 23/00 | (2006.01) |
| A61B 19/00 | (2006.01) |
| A01K 5/00 | (2006.01) |
| A01K 29/00 | (2006.01) |
| A01K 39/00 | (2006.01) |

(52) U.S. Cl. .............. 340/573.1; 340/539.1; 340/572.4; 340/693.3; 340/10.1; 128/899; 119/174; 119/51.02; 600/549

(58) Field of Classification Search ........ 340/573.1, 340/573.3, 573.4, 572.4, 10.1, 693.5, 539.1; 600/549; 128/631, 736–738, 755, 903; 119/51.02, 119/174
See application file for complete search history.

(56) References Cited

U.S. PATENT DOCUMENTS

| | | | | | |
|---|---|---|---|---|---|
| 3,781,837 | A | * | 12/1973 | Anderson et al. | ........... 600/549 |
| 4,854,328 | A | * | 8/1989 | Pollack | ........................ 600/549 |
| 5,481,262 | A | * | 1/1996 | Urbas et al. | ........... 340/870.17 |
| 5,794,625 | A | * | 8/1998 | McCarley et al. | .......... 600/549 |
| 6,317,049 | B1 | * | 11/2001 | Toubia et al. | ............. 340/573.4 |
| 6,342,839 | B1 | * | 1/2002 | Curkendall et al. | ....... 340/573.3 |
| 6,346,885 | B1 | * | 2/2002 | Curkendall | ............... 340/572.4 |
| 2002/0010390 | A1 | * | 1/2002 | Guice et al. | ................. 600/300 |

FOREIGN PATENT DOCUMENTS

GB    2308947 A   *   7/1997

* cited by examiner

*Primary Examiner*—Jeffery Hofsass
*Assistant Examiner*—Lam Pham
(74) *Attorney, Agent, or Firm*—Stites & Harbison PLLC; Jeffrey A. Haeberlin; David W. Nagle, Jr.

(57) ABSTRACT

The present invention 10 provides a system and method of monitoring and tracking a plurality of physical variables from a remote location. The invention 10 utilizes a plurality of radio frequency identification transponders 20 each coupled with a sensor for measuring physical data. The transponders 20 are powered by a radio frequency reader/interrogator 60 that provides radio frequency excitation to the transponders 20 and receives and demodulates back-scattered signals therefrom. The invention 10 is particularly advantageous in monitoring temperature in cattle herds as an aid to early diagnosis of bovine respiratory disease.

2 Claims, 2 Drawing Sheets

SYSTEM AND METHOD FOR MEASURING A PLURALITY OF PHYSICAL VARIABLES FROM A REMOTE LOCATION

CROSS-REFERENCE TO RELATED APPLICATIONS

The present application is a continuation of U.S. Utility application Ser. No. 10/086,475, now abandoned filed Mar. 1, 2002, an application claiming priority to U.S. Provisional Patent Application Ser. No. 60/272,679 entitled "Advanced Detection System for Temperature Variation" and filed Mar. 1, 2001.

BACKGROUND OF THE INVENTION

The United States Department of Agriculture reported 1999 beef sales to be in excess of $50 billion dollars. Product loss caused by deaths in the herd during the same period were 1.4% of the herd total. 61.5% of these deaths were attributable to 10 Bovine Respiratory Disease (BRD). Losses from deaths caused by BRD were estimated to be $455 million dollars in beef cattle. In addition to mortality, BRD is the major cause of sickness in feed yard cattle, with morbidity rates of 50% not uncommon.

Even when successfully treated for BRD, morbid calves experience reduced overall weight and decreased feed efficiency during the feeding period and produce a carcass with decreased grade quality for the packer. In an industry with annual sales in excess of $50 billion dollars, overall BRD losses resulting from death, treatment costs, labor, and decreased feedlot and carcass performance amount to approximately one billion dollars annually. Early detection and prevention of BRD is a major challenge and a problem for the beef industry.

Furthermore, in many animal husbandry areas such as chicken, pig and sheep farming, herd health issues can cause tremendous financial loss to farmers, brokers, and packers. Often infectious diseases having an adverse impact on herd health remain undetected until a significant portion of a herd is affected, resulting in increased treatment costs and lower value herds.

Several herd management factors contribute to the high incidence of BRD in cattle. Many calves in the U.S. have a limited vaccination program, have no pre-weaning and are taken directly from the cow to sale at a local auction barn without benefit of any prior health management program. Buyers at auction often combine calves from multiple purchase sources for shipment to feed yards. During the marketing process, calves are subjected to a variety of health stressors and are exposed to both bacterial and viral pathogens. On arrival at the feed yard, calves are typically penned and exposed to feed and water sources generally unknown to them. Unweaned calves will have little feed intake for the first few days as they often spend their time walking the pen fence and bawling. This creates additional stress in the animal and opportunity for sickness in transition.

Early intervention or mass medication of animals upon arrival at a feed yard has been shown to reduce morbidity and mortality rates from BRD for high-risk calves. Although effective, this procedure is quite expensive and results in the administration of antibiotics to many calves that don't require them. When calves contract BRD, their body temperature begins to increase measurably often days before visual symptoms are present.

SUMMARY OF THE INVENTION

The present invention offers a system to detect an increase in body temperature to provide early detection and treatment for BRD. The invention comprises a radio frequency identification device coupled with an electronic temperature sensing device forming a miniature transponder that does not require an on-board power source to supply periodic physical variable data to a reader/interrogator capable of sending and receiving radio frequency signals. When the variable being monitored is temperature, as required for diagnosis of BRD in cattle, the transponder is placed on or inside of a subject animal whereby readings of animal temperature are taken. Early diagnosis of illness in individual herd animals by monitoring temperature and administering treatment only when body temperature exceeds a predetermined value will revolutionize the methods of diagnosing and treating BRD, as well as other herd health issues capable of being diagnosed using temperature as a health baseline.

While the specific examples used throughout the specification refer to an application of the instant invention utilizing a temperature sensor to monitor animal body temperature, one of ordinary skill in the art will recognize that any of a number of physical variables may be measured and monitored using the system of the instant invention. Sensors for measuring pressure, temperature, weight, flow, acceleration, force, humidity and chemical analysis may be employed in the system of the instant invention as particular applications require.

BRIEF DESCRIPTION OF THE DRAWINGS

A better understanding of the present invention will be had upon reference to the following description in conjunction with 5 the accompanying drawings, wherein.

DETAILED DESCRIPTION OF THE PREFERRED EMBODIMENT

Figure 1:
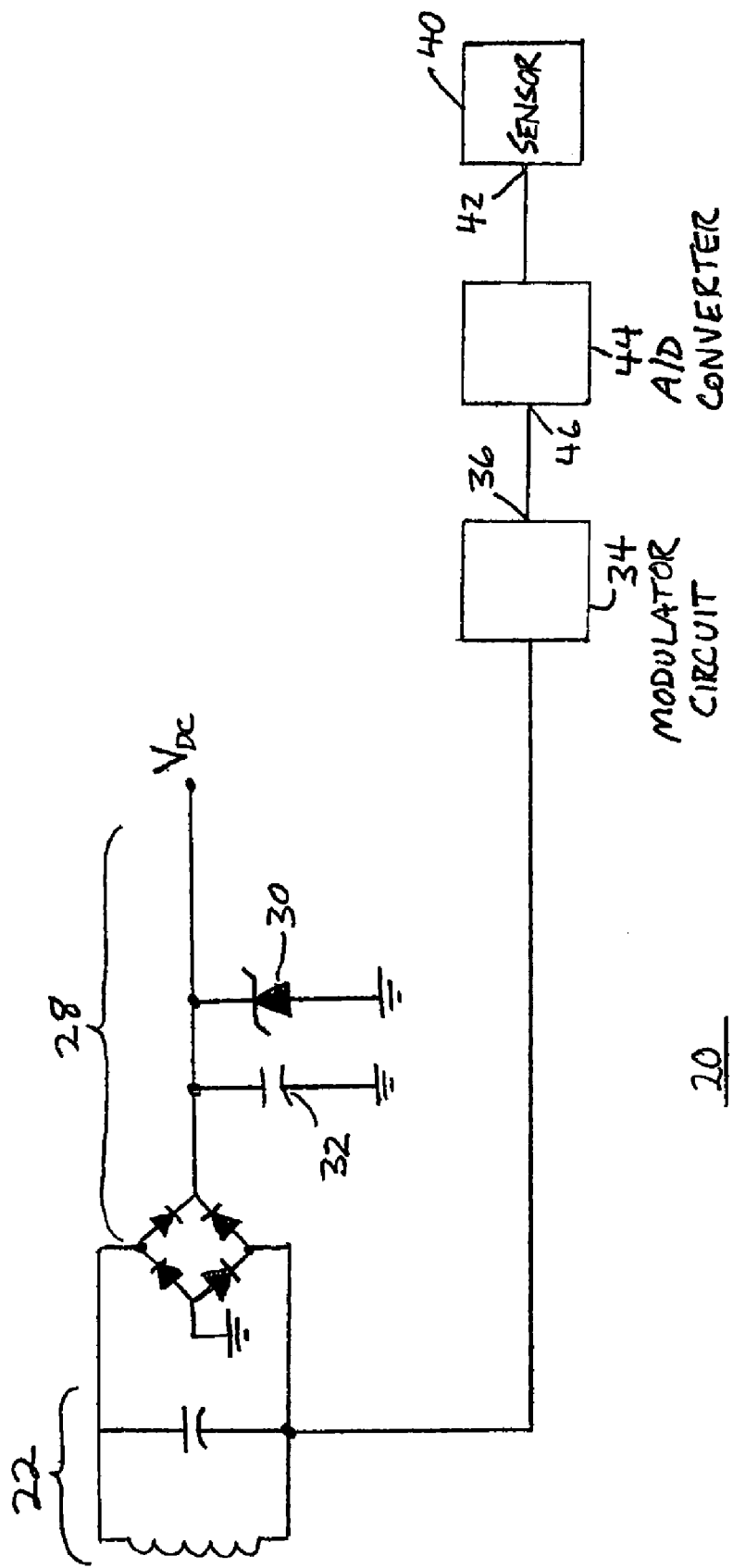
FIG. 1 is a block diagram schematic of an RFID system in accordance with the invention.
Figure 2:
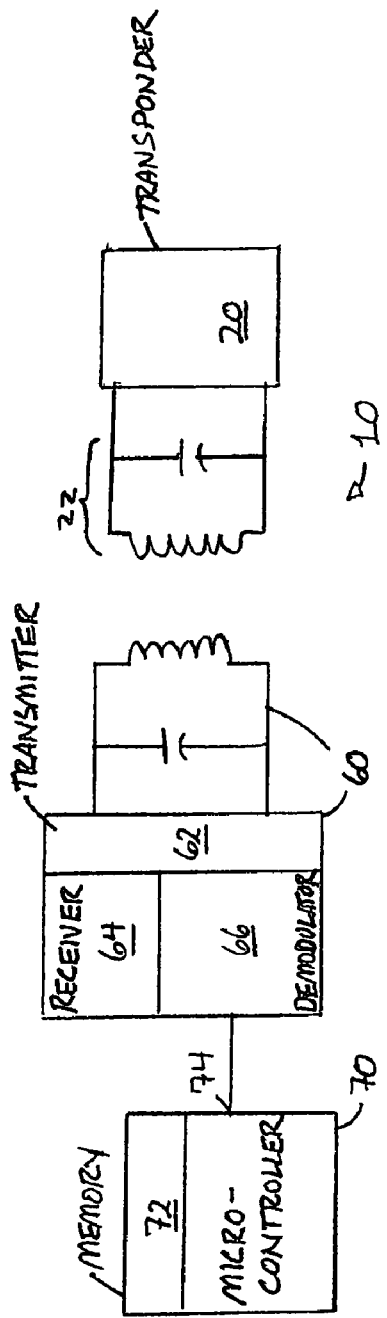
FIG. 2 is a block diagram schematic of an RFID system in accordance with the invention.
Figure 3:
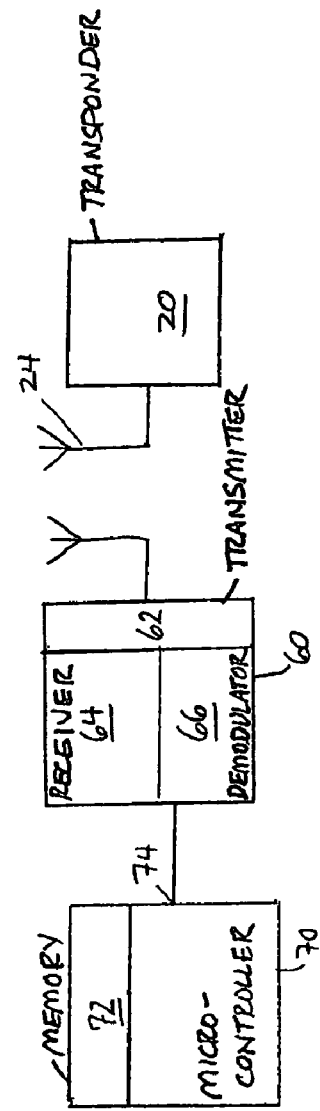
FIG. 3 is a block diagram schematic of an RFID system employing a microwave antenna in accordance with the invention.

Referring to drawing FIGS. 1, 2 and 3, and in accordance with a preferred embodiment of the instant invention, a system for measuring a physical variable 10 comprises a plurality of radio frequency identification (RFID) transponders 20, each having a unique digital identification tag and a sensor 40 coupled thereto, and at least one reader 60 (or interrogator) capable of transmitting radio frequency signals and reading said signals. The transponders 20 may be disposed at a plurality of discrete locations to allow the sensors 40 to measure a physical variable at each of the locations. The reader/interrogator pulses radio frequency (RF) signals and reads corresponding resonant RF signals from the plurality of transponders 20 representing the unique identification tag of the transponder and the value of the physical variable being measured. While the application of the system 10 of the instant invention to cattle temperature is used as an example throughout the specification, one of ordinary skill in the art will appreciate that various sensor types may be used to measure physical variables such as temperature, weight, pressure, humidity, light etc.

The transponders 20 employed in the present system 10 employ a sensor 40 to measure a physical variable, for example temperature. A plurality of known in the art sensors 40 such as thermocouples, RTD's or micro electromechanical devices may be utilized with the transponders 20. The sensors 40 produce an output signal 42 representative of the temperature detected by the sensor. The output 42 may be an analog voltage, current, frequency, or resistance, or alternatively a digital signal representative of measured temperature. In the embodiment of the invention wherein the sensor output 42 is analog, a conventional analog to digital converter 44 is used to convert the analog output 42 into a digital output 46 for further processing, as detailed below.

One embodiment of the instant invention 10 utilizes a microelectro-mechanical sensing device 40 (MEMS) to sense temperature. Known in the art MEMs devices are capable of sensing temperatures at a distance and operate on very little power, thereby enhancing the efficiency of the transponder 20 and allowing more options for placing the transponder 20 in or on an animal.

The transponder further employs a circuit 22 for receiving and resonating back radio frequency signals. The circuit 22 can be a tuned LC circuit as shown in FIGS. 1 and 2 or a microwave antenna 24 as shown in FIG. 3. The LC tank circuit may operate at a carrier frequency of, for example, 125 KHz, as is common in RFID applications. The transponder 20 further comprises a power circuit 28 utilizing a simple rectifier diode 30 and capacitor 32 to supply direct current (DC) power to the transponder components. This feature of the instant invention obviates the need to provide an on-board power source to the transponder thereby resulting in reduced weight and size, and increased device life. While the invention 10 is capable of operating without an on-board power source as described herein above, on of ordinary skill in the art will recognize that the transponder may readily be adapted to operate using a conventional direct current battery as a power source, thereby enhancing signal transmission range.

The transponder 20 also employs a conventional modulator circuit 34 having an input 36 coupled to the output 42 of the sensor 40 (or the digital output 46 of the A/D converter 44) to modulate a resonant radio frequency signal caused by a received RF signal, as discussed further below. The modulator 34 transmits the digital information from the sensor 40 as well as the unique identification data for the specific transponder to the reader/interrogator 60 utilizing back-scatter modulation.

The reader/interrogator 60 comprises a known in the art radio frequency transmitter 62 generating an RF signal at, for example, 125 KHz, and a corresponding receiver 64 to supply radio frequency signals to the plurality of transponders 20 and receive modulated signals back therefrom. A demodulator circuit 66 coupled to the receiver 64 allows the reader 60 to read the unique identification from the individual transponder 20 as well as the sensor 40 data included in the signal. The RF reader 60 is capable of demodulating a plurality of signals, thereby allowing the user to track and monitor a plurality of transponders 20 simultaneously. This feature of the invention is particularly advantageous in monitoring herd health, since transponders can be assigned or reassigned to animals in a herd as animals are added or removed therefrom.

In one embodiment of the instant invention, the reader 60 further comprises a microcontroller 70 and associated memory 72 for storing and processing the plurality of temperature data values received from the plurality of transmitters. The microcontroller 70 has an input 74 that accepts a signal from the demodulator 66 representative of the unique identification tag of the transponder and the value of the sensor reading therefrom. This information is then stored in memory 72 for further processing. The microcontroller 70 may further employ a plurality of operator interfaces, such as a mouse, keyboard, and monitor, to allow a user of the system 10 to access and process the temperature data to detect the early onset of Bovine Respiratory Disease.

In operation, the temperature sensor 40 may be placed subcutaneously in a subject animal whereby the sensed temperature value supplied by the sensor is transmitted periodically to the reader/interrogator 60 by the transponder 20. The reader 60 transmits RF signals to the transponder 20, thereby charging the power circuit 28 capacitor 32. When the capacitor is fully charged, it discharges whereupon DC power is supplied to the sensor 40, optional A/D converter 44, and modulator circuit 34. The tuned LC circuit 22 thence transmits the modulated back scattered signal back to the receiver 64 of the reader 60, where it is demodulated and stored in the microcontroller 70 memory 72 for further analysis.

The plurality of transponders 20 are also small enough to be attached to the ear of a subject animal, or any other location on an animal adjudged to be a viable sensing location, or alternatively reside permanently in the rumen thereof. An eartag application or exterior location of the instant invention allows transponders 20 to be easily removed and exchanged from one animal to another as diagnosis needs dictate.

Early identification of elevated temperatures in cattle enables detection and treatment of BRD in a much earlier stage of infection than current visual diagnostic methods. While the instant inventions' application and use is presently contemplated as being particularly useful in the early diagnosis of BRD, it is susceptible of use for monitoring temperatures in a wide variety of potential applications, for example, other farm animals such as hogs, sheep, horses, chickens, zoo animals, and human beings. The instant invention is also particularly suited for use in the dairy cow industry to identify Estrus cycles and facilitate the early diagnosis of the onset of Mastitis.

The temperature signal datum received from the plurality of transponders 20 may then be statistically analyzed to determine a baseline temperature for each subject animal and the rates of change of temperature over time. Temperature sensor 40 location will have significant impact on the data being gathered. For this reason the transponders 20 may be located at a variety of positions in or on a subject animal. The statistical analysis performed on each signal employs a correction factor to adjust for sensor 40 location in a given test subject. Sensor transponders 20 may be installed in a bovine subject at, for example, the ear canal, as an implant in the neck/shoulder area, as a tag attached to the ear, or in a bolus designed to reside in the rumen for the life of the subject animal.

The microcontroller 70 present in the reader 60 may be suitably programmed to carefully monitor temperature signals sent from each subject, and appropriately provide an alarm indication to a user if the subject animal's temperature deviates a set percentage from a predetermined temperature baseline, determined by averaging a plurality of temperature readings from a given subject over time.

While the present invention has been described in the environment of implantation in a bovine test subject, one of ordinary skill will recognize that the invention may be used to detect temperatures and variations therein in nearly any environment, including but not limited to all varieties of living organisms, for example, animals and human beings, or in any remote location.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A system for monitoring body temperatures in a plurality of herd animals, said system comprising:

a plurality of radio frequency identification transponders, each said transponder having a temperature sensor for sensing animal temperature, each herd animal provided with one of said radio frequency identification transponders, each transponder positioned such that said temperature sensor is in a viable sensing location for sensing the animal's temperature;

a reader/interrogator for:

transmitting radio frequency signals to said transponders;

receiving radio frequency signals from said transponders, said received radio frequency signals containing animal temperature data from said temperature sensors; and demodulating said received radio frequency signals into animal temperature data;

a memory for storing said animal temperature data; and a microcontroller in communication with said reader/interrogator and said memory wherein said microcontroller is for:

processing said animal temperature data and determining a baseline temperature for each animal by averaging aid temperature data for each animal over time; and providing an alarm indication when temperature data from any herd animal deviates a set percentage from said baseline temperature for said animal.

2. The system of claim 1, wherein said microcontroller is further for adjusting said temperature data by employing a correction factor to adjust for the sensor location in each animal.

* * * * *